United States Patent [19]

Kelly

[11] 4,356,167
[45] Oct. 26, 1982

[54] LIPOSOME DRUG DELIVERY SYSTEMS

[75] Inventor: Lawrence A. Kelly, Morris Plains, N.J.

[73] Assignee: Sandoz, Inc., E. Hanover, N.J.

[21] Appl. No.: 276,034

[22] Filed: Jun. 22, 1981

Related U.S. Application Data

[63] Continuation-in-part of Ser. No. 234,484, Feb. 17, 1981, abandoned, which is a continuation of Ser. No. 2,962, Jan. 12, 1979, abandoned, which is a continuation-in-part of Ser. No. 872,835, Jan. 27, 1978, abandoned.

[51] Int. Cl.$^3$ .................. A61K 9/50; A61K 37/02; A61K 37/22; B01J 13/02
[52] U.S. Cl. ........................... 424/38; 252/316; 424/178
[58] Field of Search ..................... 424/38; 252/316

[56] References Cited

U.S. PATENT DOCUMENTS

| | | | |
|---|---|---|---|
| 4,016,100 | 4/1977 | Suzuki et al. | 252/316 |
| 4,078,052 | 3/1978 | Papahadjopoulos | 252/316 X |
| 4,089,801 | 5/1978 | Schneider | 252/316 |
| 4,145,410 | 3/1979 | Sears | 252/316 X |
| 4,186,183 | 1/1980 | Steck et al. | 424/38 X |
| 4,217,344 | 8/1980 | Van Ler Berghe et al. | 252/316 X |
| 4,224,179 | 9/1980 | Schneider | 252/316 |
| 4,229,360 | 10/1980 | Schneider et al. | 252/316 X |
| 4,235,871 | 11/1980 | Papahadtopoulos et al. | 424/38 X |
| 4,241,046 | 12/1980 | Papahadtopoulos et al. | 424/38 X |
| 4,247,411 | 1/1981 | Van Ler Berghe et al. | 252/316 |

FOREIGN PATENT DOCUMENTS 2640707  3/1978  Fed. Rep. of Germany .

OTHER PUBLICATIONS

Tragl et al., Wien. Klin. Wochen Schr (1979)91(13):448–451 C.A.91# 128982T(1979).
Axt et al., Pharmazie (1979)34(5–6):350–351, C.A.91# 168852G(1979).
Hashimoto, A. et al., Endocrinol. Jpn. (1979)26(3):337–344 C.A.91# 145948D(1979).
Patel, H. et al., Biochem. Soc. Trans. (1978)6(4):784–785 C.A.90# 162383N(1979).
Patel, H. et al., Biochem. Soc. Trans. (1977)5(6):1739–1741 C.A.88# 146511F(1978).
Patel, H. et al., Febs. Lett. (1976)62(1):60–63 C.A.84# 130710B(1976).
Gebicki et al., Chem. Phys. Lipids(1976)16(2):142–160 C.A.85# 1491C(1976).
Patel, H. et al. Biochem. Soc. Trans. (1977)5(4):1054–1055 C.A.88# 16378q(1978).

*Primary Examiner*—Shep K. Rose
*Attorney, Agent, or Firm*—Gerald D. Sharkin; Robert S. Honor; Walter F. Jewell

[57] ABSTRACT

A liposome medicament delivery system wherein the medicament is encapsulated in a liposome comprising an aliphatic liquid-sterol-water lamellae. The lipid may be a sodium or potassium salt of a $C_4$ to $C_{18}$ fatty acid, and the sterol may be cholesterol.

21 Claims, 1 Drawing Figure

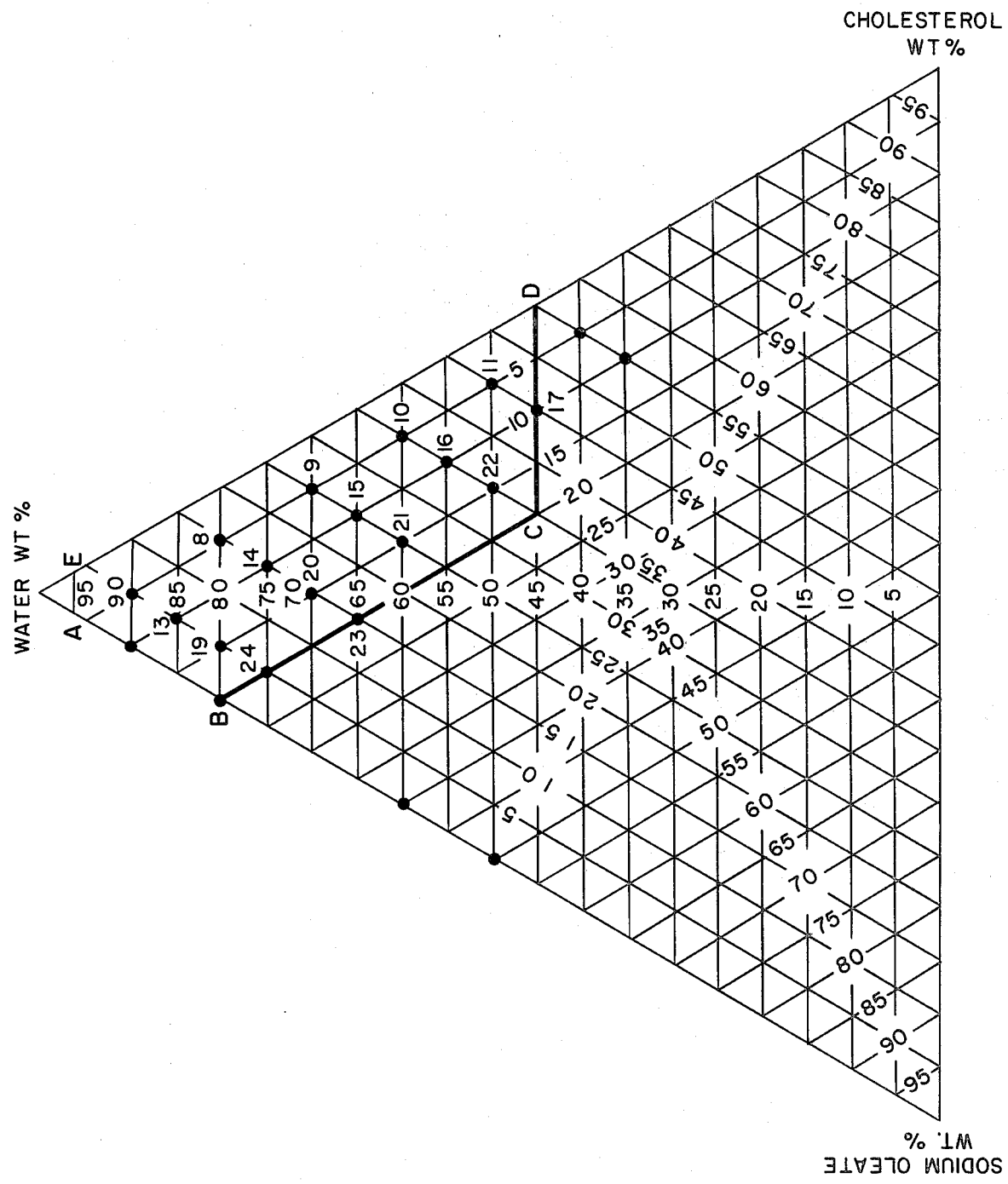

LIPOSOME DRUG DELIVERY SYSTEMS

This application is a continuation-in-part of application Ser. No. 234,484 filed Feb. 17, 1981, which in turn is a continuation of application Ser. No. 2,962 filed Jan. 12, 1979, which in turn is a continuation-in-part of application Ser. No. 872,835 filed Jan. 27, 1978, all now abandoned.

BACKGROUND OF THE INVENTION

Liquid crystalline phases of lipids are known in the prior art. These phases are called liquid crystalline since they have degrees of order which are intermediate between the three dimensional order of a crystal and the random distribution of a liquid. These phases have order in one or two dimensions characterized by onion-skin or lamellar arrangements of the lipids when dispersed in water.

When liquid crystals are subjected to energy in the form of ultrasonic radiation, they can be broken down to single layer vessicles of small dimensions called liposomes.

In recent years encapsulation of various medicaments in phospholipid-cholesterol liposomes has been accomplished. The systems described are ternary systems of a phospholipid plus cholesterol and water. Basically, these systems are prepared by dissolving the phospholipid and cholesterol in a solvent which is evaporated to leave a thin film of lipid. The aqueous phase medicament is then added, which swells the cholesterol phospholipid mixture to encapsulate the medicament. Subsequent ultrasonic irradiation provides the liposomes.

SUMMARY OF THE INVENTION

This invention relates to medicament delivery systems. It provides a liposome medicament delivery system wherein a medicament is encapsulated in a liposome comprising an aliphatic lipid-sterol-water lamellae; and processes for their preparation.

These systems may be prepared by subjecting a sterol, e.g., cholesterol crystals to an aqueous micellar solution of the aliphatic lipid and medicament, e.g., sodium oleate and medicament. After penetration of the sterol by the micelles, the resulting liquid crystals are reduced in particle size to liposomes, preferably by ultrasonic irradiation.

Alternatively, the liposomes may be prepared by the addition of the sterol to the aqueous medicament-aliphatic lipid mixture dissolved in a water missible solvent, e.g., acetone, dioxane, alcohols having 1 to 4 carbon atoms, and the like, by stirring with gentle warming (e.g., 37°–60° C.). The solvent is evaporated reducing the resultant liquid crystals to liposomes without requiring ultrasonic irradiation to produce the liposomes.

Certain medicaments may be insoluble or relatively insoluble in an aqueous micellar solution of the aliphatic lipid. In such cases, liposomes may be prepared by dissolving both the medicament and the sterol in a solvent in which both are soluble, e.g., chloroform, benzene, petroleum ethers and the like. The solvent is then removed and the resulting medicament-sterol mixture is contacted with an aqueous micellar solution of the aliphatic lipid. The resulting liquid crystals are reduced in particle size to liposomes by ultrasonic irradiation.

The penetration of the sterol occurs at concentrations above the critical micelle concentration (CMC) 1–10 mM of the aliphatic lipid. There is, therefore, a micellar system in equilibrium with the liposomes which acts to further suspend the entrapped medicament. The particle size of the liposomes of this invention is from about 10 to 600 millimicrons.

Certain medicaments in the liposome systems may be subject to alkaline degradation such as hydrolysis. Adjustment of the hydrogen ion concentration (pH) of these systems may be necessary to protect the medicaments from the alkaline degradation.

DESCRIPTION OF THE PREFERRED EMBODIMENTS

The aliphatic lipid may be any pharmacologically acceptable aliphatic surface-active compound which forms micells in aqueous media when present in concentrations above the critical micelle concentration (CMC). The aliphatic lipids of this invention are the sodium and potassium salts of $C_4$ to $C_{18}$ saturated and unsaturated fatty acids, e.g., butyric acid, isovaleric acid, caproic acid, caprylic acid, lauric acid, myristic acid, palmitic acid, stearic acid, oleic acid, linoleic acid, linolenic acid, and the like.

The sodium and potassium salts of $C_4$ to $C_{18}$ unsaturated fatty acid are preferred in the practice of this invention.

Most preferred are the sodium and potassium salts of $C_{14}$ to $C_{18}$ unsaturated fatty acids, e.g., sodium oleate and potassium oleate.

The sterols of this invention are those sterols capable of forming liposomes (as described above) with the aliphatic lipids and medicaments of this invention. Among the sterols which may be used are cholesterol, $\beta$-sitosterol, desmosterol, 7-keto-cholesterol, $\beta$-cholestanol, estradiol and the like. Cholesterol and $\beta$-sitosterol are the preferred sterols.

The nature of the medicament to be encapsulated is not critical. Suitable medicaments include vaccines and antigens, as well as drugs. Drugs useful in connection with this invention are those drugs capable of being encapsulated in an aliphatic lipid-sterol-water liposome. The drug delivery system of this invention is especially useful for intestinal absorption of labile drugs.

Among the drugs which may be used in the practice of this invention are insulin, ergot alkaloids, e.g., dihydroergocornine, dihydroergocristine, dihydroergokryptine, and mixtures thereof, thioridazine, enzymes, hormones, and the like.

Liposomes of this invention may be prepared having the following aliphatic lipid (e.g., sodium or potassium salts of $C_4$ to $C_{18}$ saturated or unsaturated fatty acid)-sterol (e.g., cholesterol)-water weight percent (%) compositions;

aliphatic lipid from about 0.03% to about 20%, sterol from about 1.0% to about 55%, and water from about 45% to about 97%.

Preferably the liposomes may contain the aliphatic lipid from about 1.0% to about 15%, sterol from about 1.0% to about 40%, and water from about 50% to about 97%.

More preferably, the liposomes may contain the aliphatic lipid from about 5.0% to about 10%, sterol from about 1.0% to about 10%, and water from about 75% to about 97%.

The processes of this invention are preferably carried out in an inert atmosphere, e.g., nitrogen, to prevent autooxidation of the lipid and/or sterol.

The processes of this invention may be carried out from a temperature (C°) at which the critical micelle concentration of the lipid is reached, to about 60° C. Preferably the processes may be carried out at from about 20° C. to about 50° C. More preferably the processes may be carried out at from 25° C. to about 45° C.

Penetration time of the aliphatic lipid-medicament micelle into the sterol liquid crystals of this invention is from about 2 minutes to one hour before sonicating.

When it is necessary to protect the medicament from alkaline degradation, the pH of the liposome system may be adjusted from an alkaline pH to a neutral or acid pH, e.g. from about pH8 to about pH5. The pH adjustment may be affected by contacting the liposome system with a pharmaceutically acceptable mineral acid, e.g. hydrochloric acid, organic acid, e.g. citric acid, or buffer solution. The liposome system may be pH treated either before or after sonication.

The liposome medicament delivery systems of this invention are useful for both oral and parenteral administration of medicaments. Oral administration is preferred, however, as the liposome encapsulation may serve to protect drugs such as insulin which are labile in the digestive system. For oral administration the liposome suspension may be admixed with pharmacologically acceptable dilutents or carriers and with conventional adjuvants such as flavorings and colorings, and administered in such forms as syrups, elixirs, capsules, tablets, etc. Suppositorial administration may also be utilized.

In this specification and claims, the following statements are descriptive of the terms indicated:

Micelle—collodial particles, consisting of oriented molecules, e.g., lipid molecules surrounding a medicament.
Liquid crystals—states of matter having characteristics of both liquids and crystalline solids. Liquid crystals are formed when the micelles of a lipid-medicament have penetrated a sterol.
Liposomes—the product of the particle size reduction of liquid crystals.
Lamellae—the layers of a liquid crystal or liposome.

EXAMPLE 1

The following compositions of sodium oleate, cholesterol and water were prepared by adding the indicated quantity of sodium oleate in water to the cholesterol crystals and equilibrating for 48 hours. The resulting compositions were examined for the development of liquid crystals. Liquid crystal micelle systems of sodium oleate-cholesterol-water were formed from the compositions falling within the area indicated by A, B, C, D, E on the phase diagram of the drawing. These compositions are Nos. 7–11, 13–17, and 19–24.

| # | % OLEATE | % WATER | GRAMS OLEATE | GRAMS WATER |
|---|---|---|---|---|
| 1 | 0 | 100 | 0 | 5 |
| 2 | 10 | 90 | .5 | 4.5 |
| 3 | 20 | 80 | 1 | 4 |
| 4 | 30 | 70 | 1.5 | 3.5 |
| 5 | 40 | 60 | 2.0 | 3 |
| 6 | 50 | 50 | 2.5 | 2.5 |

| # | % OLEATE | % CHOL | % WATER | GRAMS OLEATE | GRAMS CHOL | GRAMS WATER |
|---|---|---|---|---|---|---|
| 7 | 5 | 5 | 90 | .25 | .25 | 4.5 |
| 8 | 5 | 15 | 80 | .25 | .75 | 4 |
| 9 | 5 | 25 | 70 | .25 | 1.25 | 3.5 |
| 10 | 5 | 35 | 60 | .25 | 1.75 | 3 |
| 11 | 5 | 45 | 50 | .25 | 2.25 | 2.5 |
| 12 | 5 | 55 | 40 | .25 | 2.75 | 2 |
| 13 | 10 | 5 | 85 | .50 | .25 | 4.25 |
| 14 | 10 | 15 | 75 | .50 | .75 | 3.75 |
| 15 | 10 | 25 | 65 | .50 | 1.25 | 3.25 |
| 16 | 10 | 35 | 55 | .50 | 1.75 | 2.75 |
| 17 | 10 | 45 | 45 | .50 | 2.25 | 2.25 |
| 18 | 10 | 55 | 35 | .50 | 2.75 | 1.75 |
| 19 | 15 | 5 | 80 | .75 | .25 | 4 |
| 20 | 15 | 15 | 70 | .75 | .75 | 3.5 |
| 21 | 15 | 25 | 60 | .75 | 1.25 | 3 |
| 22 | 15 | 35 | 50 | .75 | 1.75 | 2.5 |
| 23 | 20 | 15 | 65 | 1.0 | .75 | 3.25 |
| 24 | 20 | 5 | 75 | 1.0 | .25 | 3.75 |

EXAMPLE 2

Two concentrations of insulin were prepared:

(1) 2500 international units (IU) or 102.9 mg. (Specific Activity=24.3 units/mg) was dissolved in 5 ml. of a 16 mg/ml aqueous sodium oleate solution,
(2) 1250 international units or 51.45 mg. (Specific Activity=24.3 units/mg) was also dissolved in 5 ml. of a 16 mg/ml aqueous sodium oleate solution.

Each of insulin preparations (1) and (2) were transferred to a 10 ml. beaker containing 20 mg. of cholesterol. The cholesterol was prepared by dissolving 200 mg. of cholesterol in 10 ml. of chloroform, then placing one ml. of the solution in a 10 ml. beaker and removing the solvent under nitrogen at room temperature. Each beaker was flushed with nitrogen, covered with parafin and placed in a 37° C. water bath with mild oscillation for 1 hour to allow insulin penetration of the cholesterol crystals. The liquid crystal suspensions were then sonicated for 2 one minute periods with a Biosonik IV Ultrasonic Generator by Brownwill with a 4 mm diameter probe. The beakers were placed in an ice bucket during the sonication. After sonication, the final compositions of the liposomes were:

| Composition (A) | 500 international units/ml. | insulin | = | 20.9 | mg/ml. |
|---|---|---|---|---|---|
|  |  | cholesterol | = | 4 | mg/ml. |
|  |  | sodium oleate | = | 16 | mg/ml. |
| Composition (B) | 250 international units/ml. | insulin | = | 10.4 | mg/ml. |
|  |  | cholesterol | = | 4 | mg/ml. |
|  |  | sodium oleate | = | 16 | mg/ml. |

Insulin concentration of the liposomes was 11.69%. Suspensions of the liposome compositions A and B were given orally to mice at concentrations of A-50 U/0.1 ml/10 gms. of body weight; and B-25 U/0.1 ml/10 gms of body weight. A control group received 0.5% carboxymethyl cellulose concurrently.

Composition A was diluted 1:10 for injection i.m. as a control.

After two and four hours the animals were sacrificed by anesthetizing with 85 mg/kg of sodium hexobarbital i.p. and collecting blood via cardiac puncture. The collected blood was placed in an Auto Analyzer Cup containing 0.025 cc. of heparin 1000 units/ml. The blood samples were capped, shaken, and kept in an ice bucket. Glucose was determined by the Auto Analyzer potassium ferriccyanide method No. N-2b.

Carboxymethyl cellulose given either by p.o. or i.m. route has the same effect on blood glucose. Therefore, the test materials whether given p.o. or i.m. can be related to the carboxymethyl cellulose control.

Normal fasting blood glucose levels are from 70 to 100 ml.

The results are shown in Table 1.

TABLE I

| Treatment | Route | BLOB GLUCOSE LEVELS (MG/100 ml) | | | |
|---|---|---|---|---|---|
| | | 2 Hrs. Post | % Δ | 4 Hrs. Post | % Δ |
| Control Carboxymethyl cellulose | p.o. | 75<br>73 $\bar{x}$ = 79.8<br>99 ± 6.4 S.E.M.<br>72 | — | 95<br>103 $\bar{x}$ = 103.0<br>109 ± 3.6 S.E.M.<br>107 | — |
| (A)<br>50μ/.1ml/10gm<br>body weight | p.o. | 95<br>57 $\bar{x}$ = 72.5<br>76 ± 8.5 S.E.M.<br>62 | 9 ↓<br>P = N.S. | 85<br>94 $\bar{x}$ = 75.3<br>53 ± 9.0 S.E.M.<br>69 | 27 ↓<br>P = <.05 |
| (B)<br>25μ/.1ml/10gm<br>body weight | p.o. | 59<br>73 $\bar{x}$ = 68.8<br>77 ± 4.0 S.E.M.<br>66 | 14 ↓<br>P = N.S. | 69<br>91 $\bar{x}$ = 96.0<br>117 ± 10.5 S.E.M.<br>107 | 6 ↓<br>P = N.S. |
| Iletin[1]<br>Insulin<br>.8μ/kg | i.m. | 30<br>25 $\bar{x}$ = 25.8<br>26 ± 1.7 S.E.M.<br>22 | 68 ↓<br>P = <.001 | 47<br>45 $\bar{x}$ = 47.7<br>80* ± 13.8 S.E.M.<br>51 | 54 ↓<br>P = <.001 |
| (A)<br>10μ/kg | i.m. | 29<br>20 $\bar{x}$ = 23.3<br>26 ± 2.3 S.E.M.<br>20 | 70 ↓<br>P = <.001 | 20<br>25 $\bar{x}$ = 28.3<br>32 ± 3.6 S.E.M.<br>36 | 73 ↓<br>P = <.001 |
| Bovine[2]<br>Pancreatic Insulin<br>10μ/kg | i.m. | 14<br>12 $\bar{x}$ = 14.0 ± 8<br>14 ± .8<br>16 | 82 ↓<br>P = <.001 | 37<br>10 $\bar{x}$ = 26.3<br>27 ± 5.8 S.E.M.<br>31 | 75 ↓<br>P = <.001 |

*Statistically rejected as an outlying result, by Q test.
S.E.M.—Standard Error of the Mean
$\bar{x}$ = mean
P = probability
[1]Illetin - E. Lilly
[2]Bovine - Sigma Chemical Significant reduction of the blood glucose level was seen 4 hours after oral dosing with 500 u/ml. insulin in the liposomes of this invention. Equivalent activity was seen in the i.m. route indicating that the insulin activity was not effected by incorporation into the liposomes.

EXAMPLE 3

Liposomes were prepared as described in Example 2. However, only 500 international units/ml. of insulin were used (A-Example 2). The liposomes were compared to both positively and negatively charged lecithin-cholesterol vessicles obtained from Avanti Biochemical (Birmingham, Alabama). The lecithin liposomes were prepared as described in Weissmann, G., et al., Proc. Nat. Acad. Sci. USA 72.88–92 (1975); Sessa, G. & Weissmann, G., J. Biol. Chem. 245. 3295–3301 (1970); Weissmann, G., Brand, A. & Franklin, E. C., J. Clin. Invest. 53. 536–543 (1974); and Weissmann, G. & Rita, G. A., Nature 240. 167–172 (1972).

The lecithin liposomes were equilibrated with 500 international units ml. of insulin as described in Example 2.

The liposomes of this invention and the lecithin liposomes were both tested in mice and analyzed as described in Example 2.

The results are shown in Table II.

TABLE II

| Treatment | Route | BLOOD GLUCOSE (MG/100 ML) | | | |
|---|---|---|---|---|---|
| | | 2 Hrs. Post | % Δ | 4 Hrs. Post | % Δ |
| Control Carboxymethyl cellulose | p.o. | $\bar{x}$ = 112.0<br>± 5.9 S.E.M. | — | $\bar{x}$ = 92.7<br>± 6.7 S.E.M. | — |
| (A)<br>50μ/.1ml/10gm<br>body weight | p.o. | $\bar{x}$ = 47.6<br>± 10.3 S.E.M. | 58 ↓<br>P = <.001 | $\bar{x}$ = 70.2<br>± 8.7 S.E.M. | 24 ↓<br>P = N.S. |
| L.C. (+)<br>Avanti<br>50μ/.1ml/10gm<br>body weight | p.o. | $\bar{x}$ = 105.8<br>± 17.8 S.E.M. | 17 ↓<br>P = N.S. | $\bar{x}$ = 92.8<br>± 5.8 S.E.M. | 0<br>P = N.S. |
| L.C. (−)<br>Avanti<br>50μ/.1ml/10gm<br>body weight | p.o. | $\bar{x}$ = 88.9<br>± 7.6 S.E.M. | 21 ↓<br>P = <.05 | $\bar{x}$ = 91.5<br>± 12.5 S.E.M. | 1 ↓<br>P = N.S. |
| 500 I μ<br>5μ/kg<br>body weight | i.m. | $\bar{x}$ = 24.8<br>± 2.5 S.E.M. | 78 ↓<br>P = <.001 | $\bar{x}$ = 21.0<br>± 2.7 S.E.M. | 77 ↓<br>P = <.001 |
| L.C. (+)<br>Avanti<br>5μ/kg<br>body weight<br>L.C. (−) | i.m. | $\bar{x}$ = 31.8<br>± 2.6 S.E.M. | 72 ↓<br>P = <.001 | $\bar{x}$ = 24.3<br>± 3.1 S.E.M. | 74 ↓<br>P = <.001 |

TABLE II-continued

| Treatment | Route | BLOOD GLUCOSE (MG/100 ML) | | | |
|---|---|---|---|---|---|
| | | 2 Hrs. Post | % Δ | 4 Hrs. Post | % Δ |
| Avanti 5μ/kg body weight | i.m. | x = 29.0 ± 3.5 S.E.M. | 74 ↓ P = <.001 | x = 18.3 ± 1.6 S.E.M. | 80 ↓ P = <.001 |

The results show that at both time periods the liposomes of this invention were superior to the lecithin vessicles when given p.o. All preparations are equally effective when given intramuscularly.

EXAMPLE 4

Liposomes were prepared by dissolving 20 mg. (25.3 I μ/mg) of insulin (bovine) in a solution of 0.5 gms. sodium oleate in 9 gms. of water, and then adding 0.5 gms. cholesterol crystals. The composition was allowed to equilibrate and was sonicated as described in Example 2.

The liposomes were isolated by ultrafiltration in a swinging bucket rotated at 20,000 RPM for 2 hours. A 40% sucrose underlayer was used to fill the tube.

Three fractions were isolated;

(1) a clear top layer,
(2) the liposome layer, and
(3) an infranatent above the sucrose layer.

The three fractions were tested by administration to mice at a dose of 0.1 ml. of each fraction/10 gm. of body weight. The animals weighed from 20-30 gms. and were fasted overnight prior to testing.

Each fraction had a separate control:

1st fraction—insulin in water (20 mg. insulin/9 ml. water;
2nd fraction—liposomes previously prepared without insulin, to which insulin was added prior to administration to the mice (20 mg. insulin/9 ml. liposome mixture);
3rd fraction—20 mg. insulin/9 ml. water and included the sucrose cushion to account for the effect on blood glucose.

The animals were doses orally as described in Example 2 and the results analyzed as described in Example 2. The results are as follows:

| | VALUES ARE BLOOD GLUCOSE MG/100 ML. | | |
|---|---|---|---|
| | CONTROL | FRACTION | % Δ |
| Top fraction | 152 ± 6 | 206 ± 2 | 35 ↑ |
| Liposomes | 164 ± 8 | 136 ± 14 | 17 ↓ |
| Infranate | 151 ± 16 | 173 ± 20 | 15 ↑ |

Only the liposome entrapped insulin decreases blood glucose. The other fractions tend to evaluate blood glucose.

EXAMPLE 5

Liposomes were prepared by preparing a slurry of 7.5 gm. cholesterol in 100 ml. acetone, 99 mol percent pure. The acetone was evaporated so that the cholesterol was dispersed evenly over the bottom of a 2 liter glass beaker.

An aqueous 5% sodium oleate micellar solution was prepared by dissolving 10 gm. purified sodium oleate in 200 ml. of distilled water, and then dissolving 400 mg. of HYDERGINE ®[1] in the solution. HYDERGINE concentration 2 mg/ml.

[1]dihydroergocormine mesylate, dihydroergocristine mesylate, dihydroergotcryptine, and dihydro-beta-ergocryptine; Sandoz, Inc.

One hundred and fifty (150) ml. of the aqueous sodium oleate-HYDERGINE solution was added to the 7.5 gms. of cholesterol and stirred in a closed system, flushed with nitrogen at room temperature for one hour.

The solution was then placed in an ultrafuge and rotated at 20,000 rpm's for 24 hours.

Three fractions were isolated:

(1) top clear yellow micelle layer 40% vol.
(2) middle yellowish viscous white layer 20% vol.
(3) bottom opaque white lisome layer 40% vol.

Van Urk spectrophometric assay for HYDERGINE indicated no variation in HYDERGINE concentration in the three fractions.

Van Urk assay for HYDERGINE determination:
Van Urk Reagent 70 ml. distilled water
1300 ml. sulfuric acid
2.5 gm. p-dimethylaminobenzaldehyde
4 ml. 5% ferric chloride solution.
QS 2 liters water.

Two (2) mg. HYDERGINE in 25 ml. water (standard solution).

Add 5 ml. HYDERGINE standard[1] solution to 5 ml. Van Urk reagent and react for 30 minutes then filter through Whatman No. 1 filter paper and scan 550 visible light for concentration of HYDERGINE.

[1]Sample is substituted for standard solution to get sample concentration.

Equation:

$$\frac{550 \text{ Absorbance Standard}}{\text{Milligrams per Milliter 2 mg. per ml.}} = \frac{\text{absorbance sample}}{x}$$

x = HYDERGINE concentration (mg/ml) in sample.

EXAMPLE 6

Sodium oleate and cholesterol liposomes were prepared as described in Example 1, Composition No. 7, and sonicated. The final pH of the system was 8.0. The pH of the liposome system was adjusted downward with 6 N HCL.

| Amount HCL | | Final pH | OBSERVATIONS IN THE ZEISS AXIOMAT MICROSCOPE MEASUREMENTS VIA OCULAR MICROMETER |
|---|---|---|---|
| 0 | A | 8.0 | Wide range of particle sizes with concentration between 20–30μ and 1μ |

| Amount HCL | OBSERVATIONS IN THE ZEISS AXIOMAT MICROSCOPE MEASUREMENTS VIA OCULAR MICROMETER | | |
|---|---|---|---|
| | | Final pH | |
| 15 μl | B | 7.0 | Main concentration of particle sizes around 20μ |
| 40 μl | C | 6.0 | Loss of large particles and mainly 1μ and less particles |
| 63 μl | D | 5.0 | Many large clumps of coacervated material but small particles less than 1μ |

The liposomes were stable after 48 hours dialysis against distilled water.

What is claimed is:

1. A liposome medicament delivery system comprising a medicament encapsulated in a liposome comprising an aliphatic lipid-sterol-water lamellae, wherein the aliphatic lipid is a sodium or potassium salt of a fatty acid having from 4 to 18 carbon atoms, in a lipid concentration which forms micelles above the critical micelle concentration, and wherein the sterol is present in an amount capable of being penetrated by the micelles of the aliphatic lipid.

2. The liposome medicament delivery system according to claim 1 wherein the sodium or potassium salt of the fatty acid has from 14 to 18 carbon atoms.

3. The liposome medicament delivery system according to claim 2 wherein the fatty acid salt is sodium oleate or potassium oleate.

4. The liposome delivery system according to claim 1 wherein the sterol is cholesterol.

5. The liposome medicament delivery system according to claim 4 wherein the sodium or potassium salt of the fatty acid has from about 14 to 18 carbon atoms.

6. The liposome medicament delivery system according to claim 5 wherein the fatty acid salt is sodium or potassium oleate.

7. The liposome medicament delivery system according to claim 1 wherein the weight percent composition of the liposome is from about 0.03% to about 20% aliphatic lipid, from about 1.0% to about 55% sterol, and from about 45% to about 97% water.

8. The liposome medicament delivery system according to claim 7 wherein the weight percent composition of the liposome composition is from about 1.0% to about 15% aliphatic lipid, from about 1.0% to about 40% sterol, and from about 50% to about 97% water.

9. The liposome medicament delivery system according to claim 8 wherein the weight percent composition of the liposome is from about 5.0% to about 10% aliphatic lipid, from about 1.0% to about 10% sterol and from about 75% to about 97% water.

10. The liposome medicament delivery system according to claim 4 wherein the weight percent composition of the liposome is from about 0.03% to about 20% fatty acid salt, from about 1.0% to about 55% cholesterol, and from about 45% to about 97% water.

11. The liposome medicament delivery system according to claim 10 wherein the weight percent composition of the liposome is from about 1.0% to about 15% fatty acid salt, from about 1.0% to about 40% cholesterol, and from about 50% to about 97% water.

12. The liposome medicament delivery system according to claim 11 wherein the weight percent composition of the liposome is from about 5.0% to about 10% fatty acid salt, from about 1.0% to about 10% cholesterol and from about 75% to about 97% water.

13. A process for the preparation of a liposome medicament delivery system according to claim 1 which comprises subjecting a sterol to an aqueous micellar solution of an aliphatic lipid and a medicament for a time sufficient for the micelles to penetrate the sterol and subsequently reducing the particle size of the resultant liquid crystals to form the liposome.

14. A process for the preparation of a liposome medicament delivery system according to claim 1 which comprises adding a sterol to an aqueous medicament-aliphatic lipid mixture dissolved in a solvent, reducing the resultant liquid crystals to liposomes and evaporating the solvent to recover the liposomes.

15. A process for the preparation of a liposome medicament delivery system according to claim 1 which comprises dissolving a sterol and a medicament in a mutual solvent, evaporating the solvent, contacting the resultant sterol-medicament mixture with an aqueous micellar solution of an aliphatic lipid for a time sufficient for the micells and medicament to penetrate the sterol, and subsequently reducing the particle size of the resultant liquid crystals to form the liposome.

16. The process according to claim 13 wherein the pH of the liposome system is adjusted by contacting the liposome system with a pharmaceutically acceptable mineral acid, organic acid or buffer solution.

17. The process according to claim 16 wherein the pH adjustment is affected prior to particle size reduction of the liquid crystals.

18. The process according to claim 14 wherein the pH of the liposome system is adjusted by contacting the liposome system with a pharmaceutically acceptable mineral acid, organic acid or buffer solution.

19. The process according to claim 18 wherein the pH adjustment is affected prior to particle size reduction of the liquid crystals.

20. The process according to claim 15 wherein the pH of the liposome system is adjusted by contacting the liposome system with a pharmaceutically acceptable mineral acid, organic acid or buffer solution.

21. The process according to claim 20 wherein the pH adjustment is affected prior to particle size reduction of the liquid crystals.

* * * * *